(12) United States Patent
Zhang et al.

(10) Patent No.: US 9,322,359 B2
(45) Date of Patent: Apr. 26, 2016

(54) GREEN TREATMENT PROCESS FOR CLEANING EXHAUST GAS GENERATED IN AIR OXIDATION OF BENZENE HOMOLOGS

(75) Inventors: Zhibing Zhang, Jiangsu (CN); Guannan Wang, Jiangsu (CN); Yue Dai, Jiangsu (CN); Lei Li, Jiangsu (CN); Weimin Meng, Jiangsu (JP)

(73) Assignee: NANJING UNIVERSITY (CN)

( * ) Notice: Subject to any disclaimer, the term of this patent is extended or adjusted under 35 U.S.C. 154(b) by 321 days.

(21) Appl. No.: 13/702,099

(22) PCT Filed: Mar. 11, 2011

(86) PCT No.: PCT/CN2011/071710
§ 371 (c)(1),
(2), (4) Date: Jan. 7, 2013

(87) PCT Pub. No.: WO2012/051826
PCT Pub. Date: Apr. 26, 2012

(65) Prior Publication Data
US 2013/0205771 A1    Aug. 15, 2013

(30) Foreign Application Priority Data
Oct. 20, 2010 (CN) .......................... 2010 1 0512570

(51) Int. Cl.
| | | |
|---|---|---|
| *F02G 5/02* | (2006.01) | |
| *B01D 3/00* | (2006.01) | |
| *B01D 3/06* | (2006.01) | |
| *B01D 53/00* | (2006.01) | |
| *C07C 51/16* | (2006.01) | |

(52) U.S. Cl.
CPC ...... *F02G 5/02* (2013.01); *B01D 3/007* (2013.01); *B01D 3/06* (2013.01); *B01D 53/002* (2013.01); *C07C 51/16* (2013.01); *B01D 2257/70* (2013.01)

(58) Field of Classification Search
CPC ...... B01D 2257/70; B01D 3/007; B01D 3/06; B01D 53/002; C07C 51/16; F02G 5/02
USPC .............................................. 60/531; 562/421
See application file for complete search history.

(56) References Cited

U.S. PATENT DOCUMENTS

| | | | |
|---|---|---|---|
| 5,614,159 A | 3/1997 | Modic et al. | |
| 7,213,540 B2 | 5/2007 | Lin et al. | |
| 2001/0042381 A1* | 11/2001 | Dodo et al. | .................. 62/238.3 |

FOREIGN PATENT DOCUMENTS

| | | |
|---|---|---|
| CN | 1634848 A | 7/2005 |
| CN | 1923788 A | 3/2007 |
| WO | 2012/051826 A1 | 4/2012 |

OTHER PUBLICATIONS

English language Machine translation of (CN1634848-of record) obtained from ProQuest Dialog on Jun. 23, 2015, 1-24 p.*
International Search Report; PCT/CN2011/071710; Int'l File Date: Mar. 11, 2011; Nanjing University; 5 pgs.

* cited by examiner

*Primary Examiner* — Jafar Parsa
*Assistant Examiner* — Amy C Bonaparte
(74) *Attorney, Agent, or Firm* — Schmeiser, Olsen & Watts, LLP

(57) ABSTRACT

A green treatment process for cleaning exhaust gas generated in the air oxidation of benzene homologs is disclosed. It takes the hot pressurized exhaust gas generated in the benzene homolog air oxidation process as driving power and heating source: firstly, introducing the said exhaust gas into a turbine refrigerator so that it can drive the refrigerator to generate the cooling capacity that will be utilized for condensing the gas phase in the upper part of the flash evaporator and for trapping organics entrained in the exhaust gas; then, leading the exhaust gas with lowered temperature and pressure into corresponding heat exchangers to provide a part of heating source for the flash evaporator and to preheat the reaction raw materials. Furthermore, introducing the condensed exhaust gas into a water absorption scrubber for further removal of trace organics entrained therein.

2 Claims, 1 Drawing Sheet

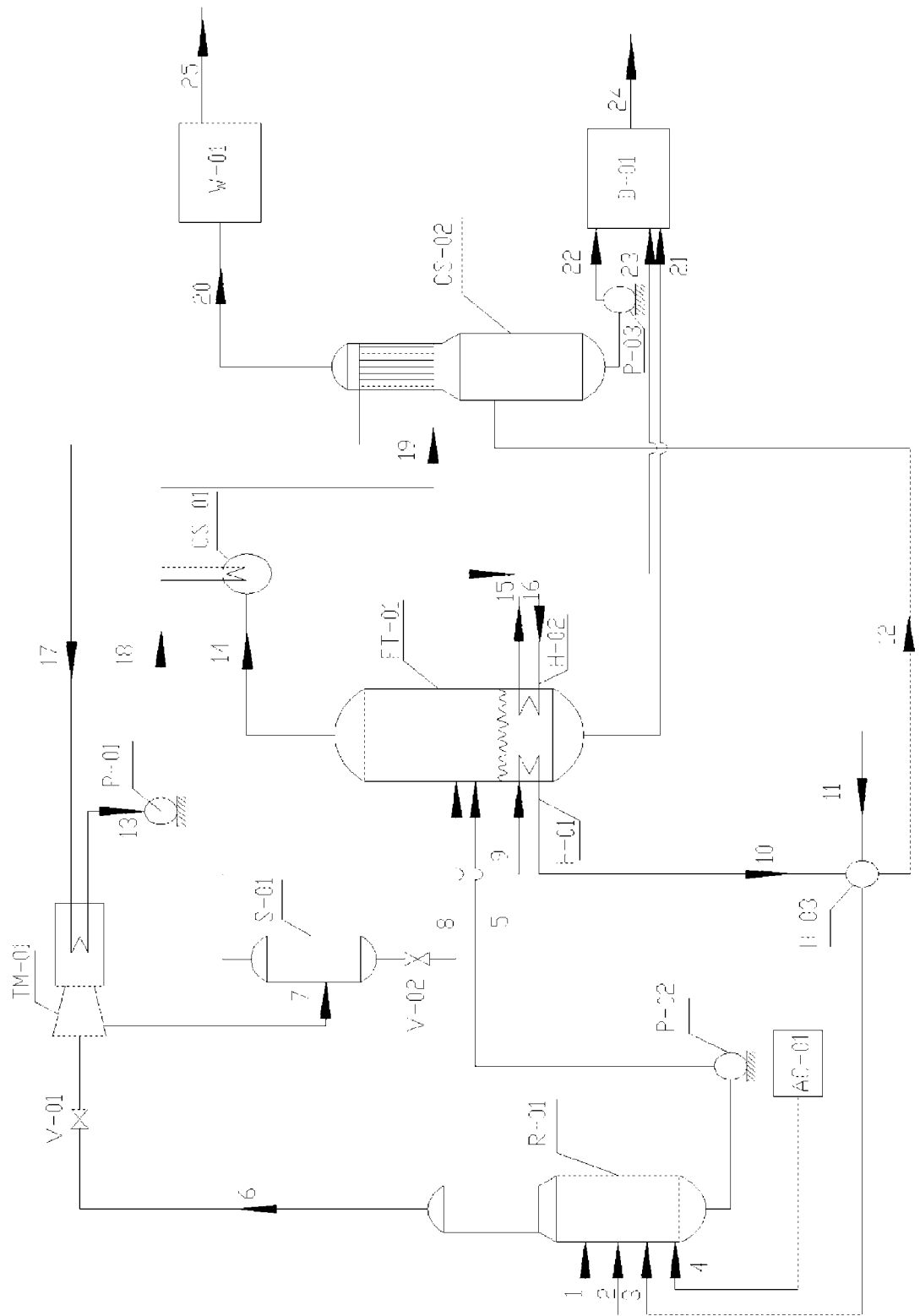

GREEN TREATMENT PROCESS FOR CLEANING EXHAUST GAS GENERATED IN AIR OXIDATION OF BENZENE HOMOLOGS

FIELD OF TECHNOLOGY

The present invention relates to a green treatment process for cleaning exhaust gas generated in air oxidation of benzene homologs.

BACKGROUND

Aromatic aldehydes or acids (for example, benzaldehyde, terephthalic acid, etc.) are important industrial chemicals. They have excellent resistance against heat and hydrolysis and are increasingly demanded in pharmaceutical industry, essence and perfume industry, plastics industry, polyester industry, special fiber industry and paint industry. Generally, the aromatic aldehydes or acids are industrially manufactured through air oxidation of benzene homologs (for example, methylbenzene, dimethylbenzene, etc.), and the manufacturing procedure can be divided into two processes: oxidation and rectification. The exhaust gas generated in the oxidation process constitutes a major source of pollution throughout the whole manufacturing procedure. On the one hand, the oxidation process requires a certain level of pressure and considerably high temperature; on the other hand, the oxidation process of hydrocarbons releases a certain amount of heat; therefore, the temperature of the discharged exhaust gas reaches as high as 120-280° C. Meanwhile, since most reactors are working under pressurized conditions, the exhaust gas discharged in the oxidation process is accordingly pressurized to some degree. Normally, the pressurized exhaust gas is about 0.3-2.8 MPa. Under such a pressurized and hot condition, the exhaust gas generated in the oxidation process unavoidably contains various amounts of reagents, solvents and products. In order to obtain up-to-standard discharge of the exhaust gas, these organic components must be removed from the exhaust gas. Currently, the process most frequently adopted in treating the exhaust gas generated in the oxidation process is as follow: firstly, trapping organic components in the exhaust gas by means of condensation realized by a condenser; next, adopting wet or dry absorption (adhesion) to remove the organic components before discharging the exhaust gas into the atmosphere. In order to conserve energy resources, the condensation process adopted by most manufacturers is realized not by refrigerating fluid, but simply by cooling water. Therefore, the temperature of the cooled exhaust gas is still as high as 50-100° C. The content of the organics contained therein still remains high. This consequently complicates the follow-up process of the wet or dry absorption (adhesion), particularly those dry absorption (adhesion) processes using active carbon, because the absorption bed formed by active carbon will soon turn saturated if the content of the organics in the exhaust gas remains high, which means that the active carbon bed must be frequently regenerated. This not only consumes a lot of energy, but also results in secondary pollution and waste of organic resources during the regeneration process.

In addition, since the exhaust gas generated in the oxidation process is pressurized, the direct discharge into the atmosphere will cause not only noise pollution but also waste of useful pressure energy.

Therefore, it is of necessity to improve the existing processes for treating the exhaust gas generated in the air oxidation of (aromatic) hydrocarbons.

SUMMARY

The present invention provides "a green treatment process for cleaning exhaust gas generated in air oxidation of benzene homologs" in order to solve the technical defects in the existing processes for treating the exhaust gas generated in the benzene homolog air oxidation process. This process can separate and recover the organic components of the exhaust gas and makes full exploitation of the thermal energy and pressure energy contained therein. Therefore, the present invention achieves goals of conserving energy resources and protecting the environment simultaneously.

As shown in FIG. 1, the green treatment process for cleaning exhaust gas generated in air oxidation of benzene homologs disclosed in the present invention consists of a start-up phase and a continuous operation phase. In the start-up phase, reagents, solvents (if needed) and catalysts are introduced into the reactor R-01 in accordance with the requirements of the oxidation process, the system is heated to the required temperature, and then air is introduced through the air compression system AC-01 into the reactor R-01 and the flow rate is controlled at the pre-set level; when the pressure in the reactor R-01 reaches the pre-set level, the exhaust gas valve V-01 at the top of the reactor R-01 is opened and the flow rate is controlled at the pre-set level so that the operating pressure of the reactor R-01 is maintained within a normal rang; with this the start-up phase comes to an end and the whole system shifts to its continuous operation phase. In the continuous operation phase, the hot pressurized exhaust gas released from the reactor R-01 is firstly introduced through the valve V-01 and corresponding pipes into a low- to medium-pressured gas turbine refrigerator TM-01 specially designed for the present invention (hereafter referred to as turbine refrigerator). The operational principle of the turbine refrigerator TM-01 is as follows: driven by the hot pressurized exhaust gas generated in the oxidation process, the turbine rotates to drive the refrigerator (essentially a common refrigerator driven by a turbine rather than an electric motor or an internal combustion engine) for refrigeration; the cooling capacity obtained thereby is transported by the coolant (salt water, ethylene glycol, etc.) into the condenser (cold trap) to provide cooling capacity for the condensation process; the said coolant is driven by the pump P-01 and establishes a circulation circuit between the condenser (cold trap) and the turbine refrigerator TM-01; the condensation process generated thereby is adopted to trap the organics entrained in the light component in the upper part of the flash evaporator FT-01 and in the exhaust gas generated in the oxidation process.

The hot pressurized exhaust gas releases energy to do work in the turbine refrigerator TM-01, and then both temperature and pressure of the exhaust gas decrease substantially; in average, the decrease of the temperature reaches 40%-50% while the decrease of the pressure reaches 50%-90%.

After coming out of the turbine refrigerator TM-01, the exhaust gas with lowered temperature and pressure is firstly introduced into the gas-liquid separator S-01 for gas-liquid separation: the gas phase is introduced through the pipe at the top of the gas-liquid separator S-01 into the coil H-01 (or heat exchangers in other forms) at the bottom of the flash evaporator FT-01, where the heat release continues; the released heat provides a part of thermal energy required by the flash evaporation process of the flash evaporator FT-01 (the rest of thermal energy required by the flash evaporation process is provided by the steam generated by another heat exchanger H-02); the temperature and the pressure of the exhaust gas are therefore further decreased; meanwhile the condensed liquid phase is collected in the gas-liquid separator S-01 and is channeled through the valve V-02 and the pipe into the flash evaporator FT-01 for flash evaporation, so that the light and heavy components of the liquid phase are separated; the exhaust gas with lowered temperature and pressure is driven by residual pressure into the heat exchanger H-03 to preheat the raw materials before the raw materials enter the reactor R-01; the thermal energy of the exhaust gas is further utilized. The exhaust gas is then introduced into the cold trap CS-02 and is cooled by the coolant therein; most of organic components entrained in the exhaust gas are condensed into liquid, and the condensed liquid is collected together and periodically pumped by the pump P-03 into the rectification system D-01 for separation and recovery. After the condensation process, the exhaust gas is channeled from the top of the cold trap CS-01 into the wet scrubber system W-01 so that the organic components entrained in the exhaust gas can be further removed; the exhaust gas treated with such a process meets the discharge standards. The exhaust gas is finally channeled out of the wet scrubber system W-01 and discharged into the atmosphere through corresponding pipes. The discharge of the exhaust gas treated thereby has no noise pollution. and organics contained therein meet relevant standards; in addition, the energy contained therein is effectively recovered for comprehensive use.

The cooling capacity generated by the turbine refrigerator TM-01 is transported by the coolant circulation pump P-01 firstly into the condenser CS-01 at the top of the flash evaporator FT-01 for heat exchange (so that the gas phase generated by flash evaporation can be condensed into liquid; the liquid obtained thereby is introduced into the rectification system for separation and purification), into the cold trap CS-02 for heat exchange, and finally back into the turbine refrigerator TM-01 for regaining cooling capacity for another round of circulation.

The technical solutions adopted in the present invention are as follows:

a green treatment process for cleaning exhaust gas generated in air oxidation of benzene homologs, comprising the following steps:

step 1. introducing reagents benzene homologs, solvents (if needed) and catalysts into a reactor R-01 in accordance with the requirements of the oxidation process, mixing the reaction system and heating said reaction system to a pre-set temperature and compressing said reaction system to a pre-set pressure, and then introducing purified air through an air compression system AC-01 into the reactor R-01 at a pre-set flow rate;

step 2. starting up the air oxidation process when the reactor R-01 reaches a pre-set level; slowly opening an exhaust gas outlet valve V-01 at the top of the reactor R-01 and controlling the emission of the exhaust gas phase generated in the air oxidation process at a certain flow rate so that the pressure in the reactor R-01 is maintained at the required operating level; transporting the product, small amounts of intermediate products, solvents and unreacted raw materials of the oxidation reaction of benzene homologs by a pump P-02 into a flash evaporator FT-01 for flash evaporation; meanwhile, introducing said gas phase, which is hot and pressurized after the air oxidation process, channeled out via the outlet at the top of the reactor R-01 into a turbine refrigerator TM-01 to drive a refrigerator for generating cooling capacity;

step 3. after doing work in the turbine refrigerator TM-01 for generating the cooling capacity, firstly introducing the hot pressurized gas phase generated in the air oxidation process into a gas-liquid separator S-01, where most of benzene organics contained therein the exhaust gas are condensed into liquid and collected in the lower part of the separator S-01; transporting the condensed liquid through corresponding valves and pipes into the flash evaporator FT-01 for separation; on the other hand, introducing the uncondensed gas phase from the gas-liquid separator S-01 through the pipe at the top of the separator S-01 into a heating coil H-01 at the bottom of the flash evaporator FT-01 so that said uncondensed gas phase from the gas-liquid separator S-01 can provide part of thermal energy required for the flash evaporation process of the flash evaporator (the rest of thermal energy is provided by the steam generated by another heat exchanger); after coming out of the heating coil H-01 at the bottom of the flash evaporator FT-01, introducing said uncondensed gas phase from the gas-liquid separator S-01 through pipes into a heat exchanger H-03 to preheat the reaction raw materials, which enables the residual heat contained in said uncondensed gas phase from the gas-liquid separator S-01 to be further utilized;

meanwhile, transporting the cooling capacity generated by the turbine refrigerator by the coolant salt water or ethylene glycol via a pump P-01 into a condenser CS-01 so that said coolant can condense the uncondensed gas phase that has been channeled out from the top outlet of said flash evaporator FT-01; introducing the liquid that is obtained through the condensation process in said condenser CS-01 through a pipe 23 into a rectification system for separation; introducing said coolant coming out of the condenser CS-01 into a cold trap CS-02 to deep freeze the uncondensed gas phase that is generated in the gas-liquid separator S-01 and has been channeled into the cold trap CS-02 via the heat exchanger H-03; where in comparison with the hot pressurized gas phase originally generated in the air oxidation process, said uncondensed gas phase out of the heat exchanger H-03 bears lowered temperature and pressure; after being further deep frozen by said coolant in the cold trap CS-02, further trapping the benzene organics entrained in said uncondensed gas phase out of the heat exchanger H-03;

if necessary, the flowing order of the said coolant into the condenser CS-01 and the cold trap CS-02 can be adjusted, namely, the coolant can flow firstly into the cold trap CS-02 and then into the condenser CS-01; such reordering of heat exchange will improve the efficiency of the cold trap CS-02 in trapping the organics entrained in the exhaust gas;

step 4. the temperature of the uncondensed gas phase from the gas-liquid separator S-01 being close to the air temperature at the outlet of the heat exchanger H-03 as the residual heat contained in said uncondensed gas phase from the gas-liquid separator S-01 has been fully utilized, where when said uncondensed gas phase from the gas-liquid separator S-01 is introduced through a pipe 12 into the cold trap CS-02 and is deep frozen below 10° C. by said coolant in the cold trap CS-02, most of benzene organics (more than 99%) in said uncondensed gas phase from the gas-liquid separator S-01 have been condensed into liquid and collected to be separated in the rectification system; subsequently, introducing the remaining gas phase that contains only a trace amount of benzene organics through a top outlet of the cold trap CS-02 into a water absorption scrubber system W-01 so that the residual benzene organics can be further removed, where the quality of the exhaust gas undergone these steps meets the discharge standards; and step 5. after the heat exchange process carried out in the cold trap CS-02, said coolant flowing out of a outlet of the cold trap CS-02 and back into the turbine refrigerator TM-01 for regaining cooling capacity for another round of circulation.

The green treatment process for cleaning exhaust gas generated in air oxidation process described above is characterized in that the said refrigeration process is realized by pressure energy; specifically speaking, the hot pressurized exhaust gas generated in the oxidation reaction is introduced into a specially designed turbine refrigerator, which, under the function of the pressurized exhaust gas, drives the refrigerator to do work for generating cooling capacity.

The present invention provides a novel, practical process for treating the exhaust gas on the basis of full consideration of the technical defects, such as heavy pollution and waste of resources, in the existing treatment processes of the exhaust gas generated in air oxidation of benzene homologs; the present invention has following prominent advantages:

(1) A turbine driven by the pressurized exhaust gas is adopted to drive a refrigerating unit so that cooling capacity is generated for condensing the gas phase created in the flash evaporation process and for cryogenically trapping the organics in the exhaust gas; such a design realizes comprehensive utilization of the pressure energy in the exhaust gas, for not only the noise pollution caused by the exhaust gas is eliminated, but also the cooling capacity generated thereby can directly trap the organics entrained in the exhaust gas with the efficiency above 99%.

(2) The high grade thermal energy generated in the oxidation process is also comprehensively utilized, and the general efficiency in utilizing energy resources is improved.

(3) After the cryogenic trapping process, the exhaust gas generated in the oxidation process is further purified by a water absorption scrubber system; the trace organics entrained in the exhaust gas is removed, and the exhaust gas meets the discharge standards and inflicts no harm to the environment.

BRIEF DESCRIPTION

FIG. 1 is a flowchart of the present invention, where:
CS-01, CS-02 cold traps, D-01 rectification system, FT-01 flash evaporator, H-01, H-02 heating coils, H-03 heat exchanger, P-01, P-02, P-03 pumps, R-01 reactor, S-01 gas-liquid separator, TM-01 turbine refrigerator, V-01, V-02 valves, W-01 water absorption scrubber system, 1-25 pipes.

DETAILED DESCRIPTION

The present invention is further illustrated by the following embodiments.

Embodiment 1

Methylbenzene and the catalyst are introduced into the reactor R-01 (1 m³ in volume) at the flow rate of 30 kg/h, the reaction system is heated to the pre-set 180° C., and then purified air is introduced through the air compression system AC-01 into the reactor R-01; when the pressure in the reactor reaches the pre-set 1.2 MPa, the valve V-01 at the top of the reactor R-01 is opened slowly, and the flow rate of the exhaust gas is controlled at the pre-set 12 m³/h to maintain the pressure required by the oxidation process. When the oxidation reaction starts up, the product benzoic acid, the solvent, small amount of the intermediate benzaldehyde and the unreacted methylbenzene are transported at the flow rate of 20 kg/h by the pump P-02 and the pipe 5 into the flash evaporator FT-01 for flash evaporation. The hot pressurized exhaust gas generated in the oxidation process is introduced into the turbine refrigerator TM-01 (KAPITSAT 7.5, JSC CRYOGENMASH) through the pipe at the top of the reactor, and drives the refrigerator (S241K, Qdrive Company) to do work for generating cooling capacity; the said cooling capacity is transported by the coolant into the cold traps CS-01 and CS-02 for respectively condensing the gas phase channeled out of the top of the flash evaporator FT-01 and the exhaust gas coming out of the heat exchanger H-03; the cool capacity then establishes a circulation circuit between the cold trap and the turbine refrigerator TM-01 through the circulation pump P-01. The temperature of the coolant can be set between −15° C. and 10° C., and may be lower if necessary. The exhaust gas is channeled out of the outlet at the top of the gas-liquid separator S-01, through the pipe 9 into the heating coil H-01 at the bottom of the flash evaporator FT-01; the heat carried by the exhaust gas provides part of the heating energy required by the flash evaporator; the rest of the heating energy the flash evaporator requires is provided by the steam generated by the heat exchanger H-02. The exhaust gas coming out of the outlet of the heating coil H-01 is driven by residual pressure into the heat exchanger H-03 to preheat the reagent methylbenzene, so that the thermal energy in the exhaust gas is further utilized. The temperature of the exhaust gas coming out of the outlet of the heat exchanger H-03 is close to the air temperature; after being introduced into the cold trap CS-02, the exhaust gas is cooled down to 0-5° C. by the freezing salt water (if necessary, the temperature can be controlled at a lower or higher degree). After the said procedures, above 99% of the reagent (methylbenzene) and the intermediate (benzaldehyde) in the exhaust gas are condensed into liquid and collected together; the collected liquid is periodically transported by the pump P-03 into the rectification system D-01 for separation and recovery. After the cryogenic treatment, the exhaust gas is introduced into the water absorption scrubber system W-01 so that the trace organics (mainly the low boiling point solvent) contained therein can be further removed. The exhaust gas treated by the whole process meets the discharge standards. The water used for absorption scrubbing in the water absorption scrubber system W-01 can be periodically channeled into a biochemical pool for treatment. In comparison with the existing treatment processes, the content of organics in the exhaust gas treated by the process disclosed herein is reduced by 80% while the efficiency in utilizing pressure energy and thermal energy is increased by 70%.

Embodiment 2

Dimethylbenzene and the catalyst are introduced into the reactor R-01 (1 m³ in volume) at the flow rate of 45 kg/h, the reaction system is heated to the pre-set 195° C., and then purified air is introduced through the air compression system AC-01 into the reactor R-01; when the pressure in the reactor reaches the pre-set 1.8 MPa, the valve V-01 at the top of the reactor R-01 is opened slowly, and the flow rate of the exhaust gas is controlled at the pre-set 12 m³/h to maintain the pressure required by the oxidation process. When the oxidation reaction starts up, the product p-xylene, the solvent, small amount of the intermediates p-carboxybenzaldehyde and p-toluic acid, and the unreacted dimethylbenzene are transported at the flow rate of 30 kg/h by the pump P-02 and the pipe 5 into the flash evaporator FT-01 for flash evaporation. The hot pressurized exhaust gas generated in the oxidation process is introduced into the turbine refrigerator TM-01 (KAPITSAT 7.5, JSC CRYOGENMASH) through the pipe at the top of the reactor, and drives the refrigerator (S241K, Qdrive Company) to do work for generating cooling capacity; the said cooling capacity is transported by the coolant into the cold traps CS-01 and CS-02 for respectively condensing the gas phase channeled out of the top of the flash evaporator FT-01 and the exhaust gas coming out of the heat exchanger H-03; the cool capacity then establishes a circulation circuit between the cold trap and the turbine refrigerator TM-01 through the circulation pump P-01. The temperature of the coolant can be set between −15° C. and 10° C., and may be lower if necessary. The exhaust gas is channeled out of the outlet at the top of the gas-liquid separator S-01, through the pipe 9 into the heating coil H-01 at the bottom of the flash evaporator FT-01; the heat carried by the exhaust gas provides part of the heating energy required by the flash evaporator; the rest of the heating energy the flash evaporator requires is provided by the steam generated by the heat exchanger H-02. The exhaust gas coming out of the outlet of the heating coil H-01 is driven by residual pressure into the heat exchanger H-03 to preheat the reagent dimethylbenzene, so that the thermal energy in the exhaust gas is further utilized. The temperature of the exhaust gas coming out of the outlet of the heat exchanger H-03 is close to the air temperature; after being introduced into the cold trap CS-02, the exhaust gas is cooled down to 0-5 □ by the freezing salt water (if necessary, the temperature can be controlled at a lower or higher degree). After the said procedures, above 99% of the reagent (dimethylbenzene) and the intermediates (p-carboxybenzaldehyde, p-toluic acid) in the exhaust gas are condensed into liquid and collected together; the collected liquid is periodically transported by the pump P-03 into the rectification system D-01 for separation and recovery. After the cryogenic treatment, the exhaust gas is introduced into the water absorption scrubber system W-01 so that the trace organics contained therein can be further removed. The exhaust gas treated by the whole process meets the discharge standards. The water used for absorption scrubbing in the water absorption scrubber system W-01 can be periodically channeled into a biochemical pool for treatment. In comparison with the existing treatment processes, the content of organics in the exhaust gas treated by the process disclosed herein is reduced by 80% while the efficiency in utilizing pressure energy and thermal energy is increased by 70%.

Embodiment 3

Unsym-trimethylbenzene and the catalyst are introduced into the reactor R-01 (1 m³ in volume) at the flow rate of 60 kg/h, the reaction system is heated to the pre-set 280° C., and then purified air is introduced through the air compression system AC-01 into the reactor R-01; when the pressure in the reactor reaches the pre-set 2.5 MPa, the valve V-01 at the top of the reactor R-01 is opened slowly, and the flow rate of the exhaust gas is controlled at the pre-set 12 m³/h to maintain the pressure required by the oxidation process. When the oxidation reaction starts up, the product trimellitic acid, the solvent, small amount of the intermediates 1,2-dimethylbenzaldehyde, 1,4-dimethylbenzaldehyde, 1,2-dimethylbenzoic acid and 1,4-dimethylbenzoic acid, and the unreacted unsym-trimethylbenzene are transported at the flow rate of 40 kg/h by the pump P-02 and the pipe 5 into the flash evaporator FT-01 for flash evaporation. The hot pressurized exhaust gas generated in the oxidation process is introduced into the turbine refrigerator TM-01 (KAPITSAT 7.5, JSC CRYOGENMASH) through the pipe at the top of the reactor and drives the refrigerator (S241K, Qdrive Company) to do work for generating cooling capacity; the said cooling capacity is transported by the coolant into the cold traps CS-01 and CS-02 for respectively condensing the gas phase channeled out of the top of the flash evaporator FT-01 and the exhaust gas coming out of the heat exchanger H-03; the cool capacity then establishes a circulation circuit between the cold trap and the turbine refrigerator TM-01 through the circulation pump P-01. The temperature of the coolant can be set between −15° C. and 10° C., and may be lower if necessary. The exhaust gas is channeled out of the outlet at the top of the gas-liquid separator S-01, through the pipe 9 into the heating coil H-01 at the bottom of the flash evaporator FT-01; the heat carried by the exhaust gas provides part of the heating energy required by the flash evaporator; the rest of the heating energy the flash evaporator requires is provided by the steam generated by the heat exchanger H-02. The exhaust gas coming out of the outlet of the heating coil H-01 is driven by residual pressure into the heat exchanger H-03 to preheat the reagent unsym-trimethylbenzene, so that the thermal energy in the exhaust gas is further utilized. The temperature of the exhaust gas coming out of the outlet of the heat exchanger H-03 is close to the air temperature; after being introduced into the cold trap CS-02, the exhaust gas is cooled down to 0-5° C. by the freezing salt water (if necessary, the temperature can be controlled at a lower or higher degree). After the said procedures, above 99% of the reagent (unsym-trimethylbenzene) and the intermediates (1, 2-dimethylbenzaldehyde, 1,4-dimethylbenzaldehyde, 1,2-dimethylbenzoic acid and 1,4-dimethylbenzoic acid) in the exhaust gas are condensed into liquid and collected together; the collected liquid is periodically transported by the pump P-03 into the rectification system D-01 for separation and recovery. After the cryogenic treatment, the exhaust gas is introduced into the water absorption scrubber system W-01 so that the trace organics contained therein can be further removed. The exhaust gas treated by the whole process meets the discharge standards. The water used for absorption scrubbing in the water absorption scrubber system W-01 can be periodically channeled into a biochemical pool for treatment. In comparison with the existing treatment processes, the content of organics in the exhaust gas treated by the process disclosed herein is reduced by 80% while the efficiency in utilizing pressure energy and thermal energy is increased by 70%.

Embodiment 4

Fluorotoluene, tetrabromoethane and the catalyst are introduced into the reactor R-01 (1 m³ in volume) at the rate of 40 kg/h, the reaction system is heated to the pre-set 190° C., and then purified air is introduced through the air compression system AC-01 into the reactor R-01; when the pressure in the reactor reaches the pre-set 1.5 MPa, the valve V-01 at the top of the reactor R-01 is opened slowly, and controlling the flow rate of the exhaust gas at the pre-set 12 m³/h to maintain the pressure required by the oxidation process. When the oxidation reaction starts up, the products fluorotoluene and tetrabromoethane, small amount of the intermediates fluorobenzaldehyde and fluorobenzoic acid, and the unreacted fluorotoluene are transported at the flow rate of 25 kg/h by the pump P-02 and the pipe 5 into the flash evaporator FT-01 for flash evaporation. The hot pressurized exhaust gas generated in the oxidation process is introduced into the turbine refrigerator TM-01 (KAPITSAT 7.5, JSC CRYOGENMASH) through the pipe at the top of the reactor and drives the refrigerator (S241K, Qdrive Company) to do work for generating cooling capacity; the said cooling capacity is transported by the coolant into the cold traps CS-01 and CS-02 for respectively condensing the gas phase channeled out of the top of the flash evaporator FT-01 and the exhaust gas coming out of the heat exchanger H-03; the cool capacity then establishes a circulation circuit between the cold trap and the turbine refrigerator TM-01 through the circulation pump P-01. The temperature of the coolant can be set between −15°

C. and 10° C., and may lower if necessary. The exhaust gas is channeled out of the outlet at the top of the gas-liquid separator S-01, through the pipe 9 into the heating coil H-01 at the bottom of the flash evaporator FT-01; the heat carried by the exhaust gas provides part of the heating energy required by the flash evaporator; the rest of the heating energy the flash evaporator requires is provided by the steam generated by the heat exchanger H-02. The exhaust gas coming out of the outlet of the heating coil H-01 is driven by residual pressure into the heat exchanger H-03 to preheat the reagent fluorotoluene, so that the thermal energy in the exhaust gas is further utilized. The temperature of the exhaust gas coming out of the outlet of the heat exchanger H-03 is close to the air temperature; after being introduced into the cold trap CS-02, the exhaust gas is cooled down to 0-5° C. by the freezing salt water (if necessary, the temperature can be controlled at a lower or higher degree). After the said procedures, above 99% of the reagent (fluorotoluene) and the intermediates (fluorobenzaldehyde and fluorobenzoic acid) in the exhaust gas are condensed into liquid and collected together; the collected liquid is periodically transported by the pump P-03 into the rectification system D-01 for separation and recovery. After the cryogenic treatment, the exhaust gas is introduced into the water absorption scrubber system W-01 so that the trace organics contained therein can be further removed. The exhaust gas treated by the whole process meets the discharge standards. The water used for absorption scrubbing in the water absorption scrubber system W-01 can be periodically channeled into a biochemical pool for treatment. In comparison with the existing treatment processes, the content of organics in the exhaust gas treated by the process disclosed herein is reduced by 80% while the efficiency in utilizing pressure energy and thermal energy is increased by 70%.

Embodiment 5 m-xylene and the catalyst are introduced into the reactor R-01 (1 m³ in volume) at the flow rate of 55 kg/h, the reaction system is heated to the pre-set 200° C., and then the purified air is introduced through the air compression system AC-01 into the reactor R-01; when the pressure in the reactor reaches the pre-set 2.3 MPa, the valve V-01 at the top of the reactor R-01 is opened slowly, and the flow rate of the exhaust gas is controlled at the pre-set 12 m³/h to maintain the pressure required by the oxidation process. When the oxidation reaction starts up, the product m-methylbenzoic acid, the solvent, small amount of the intermediate m-tolualdehyde, and the unreacted m-xylene are transported at the flow rate of 36 kg/h by the pump P-02 and the pipe 5 into the flash evaporator FT-02 for flash evaporation. The hot pressurized exhaust gas generated in the oxidation process is introduced into the turbine refrigerator TM-01 (KAPITSAT 7.5, JSC CRYOGENMASH) through the pipe at the top of the reactor, and drives the refrigerator (S241K, Qdrive Company) to do work for generating cooling capacity; the said cooling capacity is transported by the coolant into the cold traps CS-01 and CS-02 for respectively condensing the gas phase channeled out of the top of the flash evaporator FT-01 and the exhaust gas coming out of the heat exchanger H-03; the cool capacity then establishes a circulation circuit between the cold trap and the turbine refrigerator TM-01 through the circulation pump P-01. The temperature of the coolant can be set between −15° C. and 10° C., and may be lower if necessary. The exhaust gas is channeled out of the outlet at the top of the gas-liquid separator S-01, through the pipe 9 into the heating coil H-01 at the bottom of the flash evaporator FT-01; the heat carried by the exhaust gas provides part of the heating energy required by the flash evaporator; the rest of the heating energy the flash evaporator requires is provided by the steam generated by the heat exchanger H-02. The exhaust gas coming out of the outlet of the heating coil H-01 is driven by residual pressure into the heat exchanger H-03 to preheat the reagent m-xylene, so that the thermal energy in the exhaust gas is further utilized. The temperature of the exhaust gas coming out of the outlet of the heat exchanger H-03 is close to the air temperature; after being introduced into the cold trap CS-02, the exhaust gas is cooled down to 0-5° C. by the freezing salt water (if necessary, the temperature can be controlled at a lower or higher degree). After the said procedures, above 99% of the reagent (m-xylene) and the intermediates (m-tolualdehyde) in the exhaust gas are condensed into liquid and collected together; the collected liquid is periodically transported by the pump P-03 into the rectification system D-01 for separation and recovery. After the cryogenic treatment, the exhaust gas is introduced into the water absorption scrubber system W-01 so that the trace organics contained therein can be further removed. The exhaust gas treated by said whole process meets the discharge standards. The water used for absorption scrubbing in the water absorption scrubber system W-01 can be periodically channeled into a biochemical pool for treatment. In comparison with the existing treatment processes, the content of organics in the exhaust gas treated by the process disclosed herein is reduced by 80% while the efficiency in utilizing pressure energy and thermal energy is increased by 70%.

Embodiment 6 p-xylene, acetic acid and the catalyst are introduced into the reactor R-01 (1 m³ in volume) at the rate of 50 kg/h, the reaction system is heated to the pre-set 220° C., and then purified air is introduced through the air compression system AC-01 into the reactor R-01; when the pressure in the reactor reaches the pre-set 2.0 MPa, the valve V-01 at the top of the reactor R-01 is opened slowly, and the flow rate of the exhaust gas is controlled at the pre-set 12 m³/h to maintain the pressure required by the oxidation process. When the oxidation reaction starts up, the product terephthalic acid, the solvent, small amount of the intermediates p-methylbenzaldehyde, p-toluic acid and p-phthalaldehyde, and the unreacted p-xylene are transported at the flow rate of 33 kg/h by the pump P-02 and the pipe 5 into the flash evaporator FT-01 for flash evaporation. The hot pressurized exhaust gas generated in the oxidation process is introduced into the turbine refrigerator TM-01 (KAPITSAT 7.5, JSC CRYOGENMASH) through the pipe at the top of the reactor, and drives the refrigerator (S241K, Qdrive Company) to do work for generating cooling capacity; the said cooling capacity is transported by the coolant into the cold traps CS-01 and CS-02 for respectively condensing the gas phase channeled out of the top of the flash evaporator FT-01 and the exhaust gas coming out of the heat exchanger H-03; the cool capacity then establishes a circulation circuit between the cold trap and the turbine refrigerator TM-01 through the circulation pump P-01. The temperature of the coolant can be set between −15° C. and 10° C., and may be lower if necessary. The exhaust gas is channeled out of the outlet at the top of the gas-liquid separator S-01, through the pipe 9 into the heating coil H-01 at the bottom of the flash evaporator FT-01; the heat carried by the exhaust gas provides part of the heating energy required by the flash evaporator; the rest of the heating energy the flash evaporator requires is provided by the steam generated by the heat exchanger H-02. The exhaust gas coming out of the outlet of the heating coil H-01 is driven by residual pressure into the heat exchanger H-03 to preheat the reagent p-xylene, so that the thermal energy in the exhaust gas is further utilized. The temperature of the exhaust gas coming out of the outlet of the heat exchanger H-03 is close to the air temperature; after being introduced into the cold trap CS-02, the exhaust gas is cooled down to 0-5° C. by the freezing salt water (if necessary, the temperature can be controlled at a lower or higher degree). After the said procedures, above 99% of the reagent (p-xylene) and the intermediates (p-methylbenzaldehyde, p-toluic acid and p-phthalaldehyde) in the exhaust gas are condensed into liquid and collected together; the collected liquid is periodically transported by the pump P-03 into the rectification system D-01 for separation and recovery. After the cryogenic treatment, the exhaust gas is introduced into the water absorption scrubber system W-01 so that the trace organics contained therein can be further removed. The exhaust gas treated by the whole process meets the discharge standards. The water used for absorption scrubbing in the water absorption scrubber system W-01 can be periodically channeled into a biochemical pool for treatment. In comparison with the existing treatment processes, the content of organics in the exhaust gas treated by the process disclosed herein is reduced by 80% while the efficiency in utilizing pressure energy and thermal energy is increased by 70%.

What is claimed is:

1. A green treatment process for cleaning exhaust gas generated in air oxidation of benzene homologs comprising the following steps:

step 1. introducing benzene homologs, solvents and catalysts into a reactor in accordance with the requirements of an oxidation process, mixing the benzene homologs, solvents and catalysts and heating the benzene homologs, solvents and catalysts to a pre-set temperature and compressing the benzene homologs, solvents and catalysts to a pre-set pressure, and then introducing purified air through an air compression system into the reactor at a pre-set flow rate;

step 2. starting up an air oxidation process of benzene homologs when the reactor reaches the pre-set pressure; opening an exhaust gas outlet valve at a top of the reactor and controlling the emission of a gas phase generated in the air oxidation process at a certain flow rate so that the pressure in the reactor is maintained at a required operating level; transporting a product, of intermediate products, solvents and unreacted raw materials of the air oxidation process of benzene homologs by a pump into a flash evaporator for flash evaporation; introducing said gas phase, which is hot and pressurized after the air oxidation process, channeled out via the outlet at the top of the reactor into a turbine refrigerator to drive the turbine refrigerator for generating a cooling capacity;

step 3. after doing work in the turbine refrigerator for generating the cooling capacity, firstly introducing the hot pressurized gas phase into a gas-liquid separator, wherein most of the benzene organics contained therein condensed into liquid and collected in a lower part of a separator; transporting the condensed liquid through corresponding valves and pipes into the flash evaporator for separation; introducing the uncondensed gas phase from the gas-liquid separator through a pipe at a top of the separator into a heating coil at a bottom of the flash evaporator so that said uncondensed gas phase from the gas-liquid separator provides part of thermal energy required for the flash evaporation process of the flash evaporator; after coming out of the heating coil at the bottom of the flash evaporator, introducing the gas phase from the gas-liquid separator through pipes into a heat exchanger to preheat the reaction raw materials, which enables the residual heat contained in said uncondensed gas phase from the gas-liquid separator to be further utilized;

meanwhile, transporting the cooling capacity generated by the turbine refrigerator by a coolant, wherein the coolant is salt water or ethylene glycol, via a pump into a condenser so that said coolant can condense an uncondensed gas phase that has been channeled out from a top outlet of the flash evaporator; introducing the liquid that is obtained through the condensation process in said condenser through a pipe into a rectification system for separation; the coolant coming out from the condenser is then introduced into a cold trap to deep freeze the uncondensed gas phase that is generated in the gas-liquid separator and has been channeled into the cold trap via the heat exchanger; wherein in comparison with the hot pressurized gas phase originally generated in the air oxidation process, said uncondensed gas phase out of the heat exchanger bears lowered temperature and pressure; after being further deep frozen by said coolant in the cold trap, further trapping the benzene organics entrained in said uncondensed gas phase out of the heat exchanger;

step 4. the temperature of the uncondensed gas phase from the gas liquid separator being close to the air temperature at the outlet of the heat exchanger as the residual heat contained in said uncondensed gas phase from the gas-liquid separator has been fully utilized; wherein when the uncondensed gas phase from the gas-liquid separator is introduced through a pipe into the cold trap and is cryogenically frozen below 10° C. by the coolant in the cold trap, more than 99% of the benzene organics in the uncondensed gas phase from the gas-liquid separator have been condensed into liquid and collected to be separated in the rectification system; subsequently, introducing the remaining gas phase that contains only a trace amount of benzene organics through a top outlet of the cold trap into a water absorption scrubber system so that the residual benzene organics can be further removed; and step 5. after the heat exchange process carried out in the cold trap, flowing the coolant out of a outlet of the cold trap and back into the turbine refrigerator for regaining cooling capacity for another round of circulation.

2. A green treatment process for cleaning exhaust gas generated in air oxidation process of benzene homologs as defined in claim 1, wherein the refrigeration process is operated by pressure energy; wherein the hot pressurized exhaust gas generated in the air oxidation reaction is introduced into a specially designed turbine, which, under the function of the pressurized exhaust gas, drives the refrigerator to do work for generating cooling capacity.

* * * * *